(12) United States Patent
Gochanour

(10) Patent No.: US 7,703,647 B2
(45) Date of Patent: Apr. 27, 2010

(54) DISPENSER FOR FLEXIBLE THIN-FILM HAND COVERINGS

(76) Inventor: G. Gary Gochanour, 3108 Baker Rd., Dexter, MI (US) 48130

( * ) Notice: Subject to any disclaimer, the term of this patent is extended or adjusted under 35 U.S.C. 154(b) by 1580 days.

(21) Appl. No.: 10/686,298

(22) Filed: Oct. 15, 2003

(65) Prior Publication Data

US 2004/0074941 A1 Apr. 22, 2004

Related U.S. Application Data

(60) Provisional application No. 60/418,681, filed on Oct. 15, 2002.

(51) Int. Cl.
*B25C 11/02* (2006.01)
(52) U.S. Cl. .................. 225/90; 225/54; 156/510; 128/879; 226/172
(58) Field of Classification Search ............ 225/10–16, 225/47, 90–91, 20, 54, 76, 85, 51; 83/649, 83/650, 620, 614; 221/230, 282, 70, 186, 221/187, 190, 30–34; 242/590–598.5, 391.3, 242/557; 128/877–879; 156/510; 312/34.16; 206/411; 602/20–21; 426/106; 271/272; 226/172; 26/88
See application file for complete search history.

(56) References Cited

U.S. PATENT DOCUMENTS

| | | | |
|---|---|---|---|
| 356,385 A | 1/1887 | Waterhouse | |
| 526,038 A | 9/1894 | Hoke | 225/89 |
| 767,233 A | 8/1904 | McCourt | |
| 1,332,194 A | 3/1920 | Arcus | |
| 1,486,006 A | 12/1924 | Blom | |
| 1,731,340 A | 10/1929 | Lambert | 2/158 |
| 2,311,363 A | 2/1943 | Bevier | 164/84.5 |
| 2,576,404 A | 11/1951 | Krueger | 242/55.5 |
| 2,577,284 A | 12/1951 | Steinle | 2/169 |
| 2,617,198 A | 11/1952 | Sharpe | 225/14 |
| 2,751,592 A | 6/1956 | Longstreth et al. | 2/21 |
| 2,773,264 A | 6/1956 | Nover | 2/159 |
| 2,864,090 A | 12/1958 | Sutherland | 2/161.7 |
| 2,954,910 A | 10/1960 | Moncrieff | 225/20 |
| 3,035,345 A | 5/1962 | Barnard | 225/14 |
| 3,229,875 A | 1/1966 | Stoller | 2/169 |
| 3,260,260 A | 7/1966 | Questel | 128/132 |

(Continued)

FOREIGN PATENT DOCUMENTS

DE 4135973 5/1993 ............ 2/16

(Continued)

*Primary Examiner*—Boyer D. Ashley
*Assistant Examiner*—Laura M. Lee
(74) *Attorney, Agent, or Firm*—Gifford, Krass, Sprinkle, Anderson & Citkowski, P.C.

(57) ABSTRACT

An improved dispenser for thin, flexible hand coverings includes a unique mechanism to retain the opposing edges of the flexible film as it is advanced and applied to the hand, thereby promoting a controlled stretching, adherence and release. In the preferred embodiment, the entrapment of the film edges is carried out using interlocking chains that advance through guide channels. Another improvement is that the housing of the dispenser in this case is raised as the user pulls down the film to be adhered, and it is the weight of the dispenser that causes the unit to reset for the next use, thereby eliminating the need for springs, at least for this purpose.

8 Claims, 5 Drawing Sheets

U.S. PATENT DOCUMENTS

| | | | |
|---|---|---|---|
| 3,387,307 A | 6/1968 | Blatz | 2/167 |
| 3,554,419 A * | 1/1971 | Robinson et al. | 225/93 |
| 3,645,835 A | 2/1972 | Hodgson | 161/146 |
| 3,821,915 A * | 7/1974 | Larrable | 83/174 |
| 3,989,175 A | 11/1976 | Cherrin | 225/46 |
| 4,017,907 A | 4/1977 | Margolis | 2/158 |
| 4,034,853 A | 7/1977 | Smith | 2/169 |
| 4,212,217 A * | 7/1980 | Heppner | 83/277 |
| 4,347,931 A | 9/1982 | Ginger et al. | 206/438 |
| 4,364,501 A | 12/1982 | Curtiss, Jr. | 225/19 |
| 4,454,974 A | 6/1984 | Cooke | 225/106 |
| 4,607,774 A | 8/1986 | Garr | 225/47 |
| 4,773,532 A * | 9/1988 | Stephenson | 206/278 |
| 4,804,432 A | 2/1989 | Jurrius et al. | 156/380 |
| 4,832,650 A | 5/1989 | Tong | |
| 4,844,293 A | 7/1989 | McLaughlin | 221/34 |
| 4,847,918 A | 7/1989 | Sturm | 2/161 |
| 4,884,300 A | 12/1989 | Vistins | 2/162 |
| 4,913,897 A | 4/1990 | Chvapil et al. | 424/99 |
| 4,916,757 A | 4/1990 | Berlin et al. | 2/159 |
| 4,928,322 A | 5/1990 | Bradfield | 2/169 |
| 4,938,515 A | 7/1990 | Fazio | 2/21 |
| 4,942,992 A | 7/1990 | Fischer et al. | 224/240 |
| 4,951,858 A | 8/1990 | Krall | 225/77 |
| 4,993,589 A | 2/1991 | McLaughlin | 221/33 |
| 5,012,801 A | 5/1991 | Feret | 128/155 |
| 5,018,516 A | 5/1991 | Gilman | 128/155 |
| 5,020,160 A | 6/1991 | Cano | 2/159 |
| 5,024,217 A | 6/1991 | Spencer | 128/82 |
| 5,025,503 A | 6/1991 | O'Brien | 2/169 |
| 5,084,927 A | 2/1992 | Parkevich | 5/484 |
| 5,096,089 A | 3/1992 | McLaughlin | 221/26 |
| 5,172,424 A | 12/1992 | Adkins | 2/21 |
| 5,180,605 A | 1/1993 | Milner | 427/2 |
| 5,181,276 A | 1/1993 | Kersten et al. | 2/161 R |
| 5,190,197 A | 3/1993 | Novak | 224/312 |
| 5,210,880 A | 5/1993 | Yale | 2/159 |
| 5,238,641 A * | 8/1993 | Smith | 264/280 |
| 5,322,201 A | 6/1994 | Garr | 225/47 |
| 5,365,816 A * | 11/1994 | Rudy | 83/177 |
| 5,456,354 A | 10/1995 | Wood | 206/278 |
| 5,517,737 A * | 5/1996 | Viltro et al. | 26/88 |
| 5,534,346 A | 7/1996 | Robinson | 428/343 |
| 5,552,201 A | 9/1996 | Burgess et al. | 428/43 |
| 5,566,390 A | 10/1996 | Clancy | 2/16 |
| 5,573,168 A | 11/1996 | Kannankeril et al. | 225/46 |
| 5,575,014 A | 11/1996 | Kane et al. | 2/16 |
| 5,636,406 A | 6/1997 | Strong | 15/227 |
| 5,651,487 A | 7/1997 | Hansen | 225/106 |
| 5,691,069 A | 11/1997 | Lee | 428/500 |
| 5,768,968 A * | 6/1998 | Park et al. | 83/614 |
| 5,774,889 A | 7/1998 | Gochanour | 2/16 |
| 5,799,331 A | 9/1998 | Stewart | 2/158 |
| 5,864,883 A | 2/1999 | Reo | 2/158 |
| 5,878,909 A | 3/1999 | Rogow | 221/45 |
| 5,921,434 A | 7/1999 | Hollander et al. | 221/34 |
| 5,927,543 A * | 7/1999 | Dejardin et al. | 221/56 |
| 5,966,741 A | 10/1999 | Klecina | 2/169 |
| 5,975,083 A | 11/1999 | Henderson, Jr. | 128/878 |
| 6,021,919 A | 2/2000 | Kelly | 221/25 |
| 6,021,920 A | 2/2000 | Aldape | 221/96 |
| 6,112,936 A | 9/2000 | Arizmendi | 221/45 |
| 6,375,034 B1 * | 4/2002 | Corbett | 221/46 |
| 6,497,340 B2 | 12/2002 | Grinberg | 221/45 |
| 6,604,660 B2 | 8/2003 | Gochanour | 225/90 |
| 6,749,097 B1 * | 6/2004 | McElhinny | 225/20 |
| 7,082,979 B2 * | 8/2006 | Stork | 156/555 |
| 2002/0073821 A1 * | 6/2002 | Broehl | 83/436.15 |
| 2004/0000572 A1 * | 1/2004 | Engelhardt et al. | 225/1 |
| 2004/0082454 A1 * | 4/2004 | White et al. | 493/189 |

FOREIGN PATENT DOCUMENTS

| | | | |
|---|---|---|---|
| FR | 2542980 | 9/1984 | 2/158 |
| WO | WO89/00385 | 9/1989 | 2/16 |

* cited by examiner

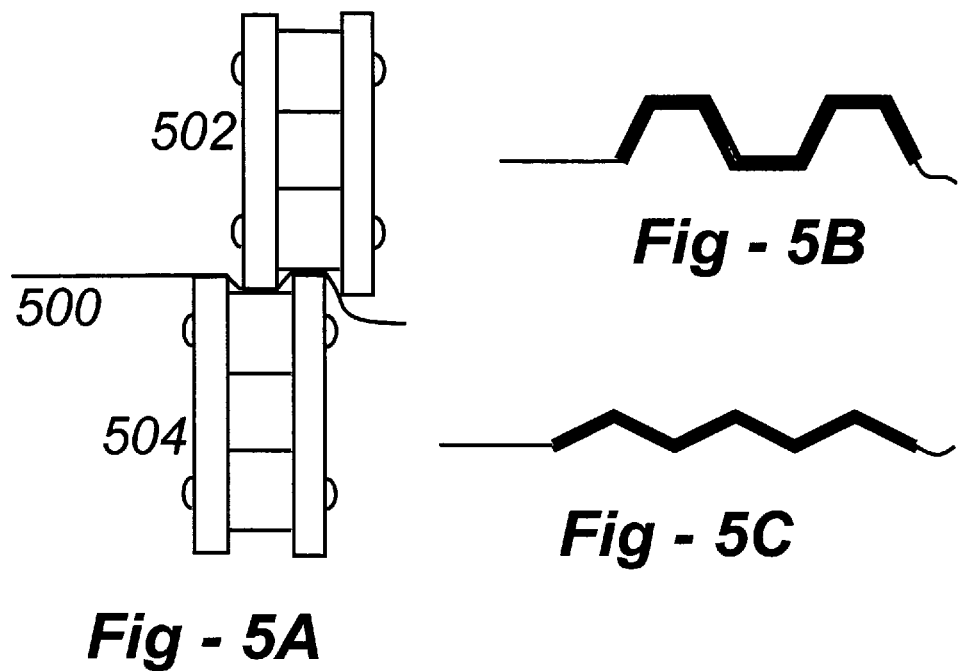
*Fig - 5A*
*Fig - 5B*
*Fig - 5C*
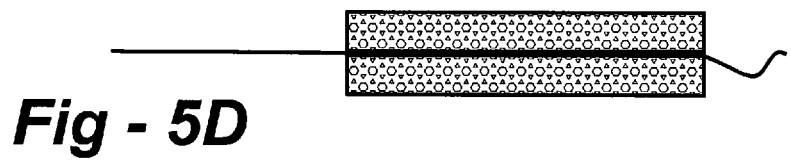
*Fig - 5D*
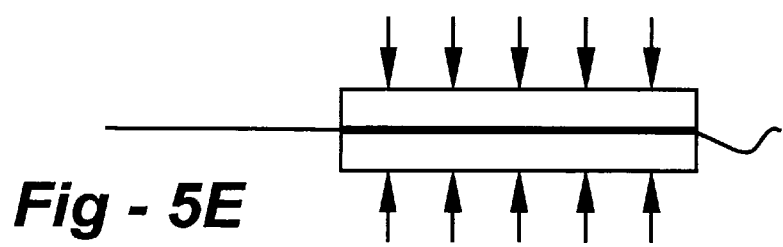
*Fig - 5E*

DISPENSER FOR FLEXIBLE THIN-FILM HAND COVERINGS

REFERENCE TO RELATED APPLICATION

This application claims priority from U.S. Provisional Patent Application Ser. No. 60/418,681, filed Oct. 15, 2002, the entire content of which is incorporated herein by reference.

FIELD OF THE INVENTION

This invention is related to protective hand coverings and, more particularly, to a dispenser for a protective hand covering formed from a sheet of thin flexible film which is temporarily bonded to a user's hand during use.

BACKGROUND OF THE INVENTION

In many fields, such as the dental, medical, food service, laboratory, and precision manufacturing fields, reducing the potential for contamination is a primary concern. Because workers in these fields routinely manually handle contaminated or contaminatable materials, it is critical that some type of barrier be interposed between the hands of the workers and the contaminated or contaminatable materials. Typically, this barrier comprises a latex or plastic film glove or mitten. The user places their hand into the glove or mitten prior to handling the contaminated or contaminatable materials and this prevents contamination from being transferred to or from the substance or object being handled.

There are primarily three routes for the transfer of contaminates. The first route is the transfer of contaminates from the contaminated material to the user handling the contaminated material. In the dental, medical and other health care fields, the AIDS epidemic has heightened awareness of the possibility of patients infecting their health care workers with the HIV virus through exposure to body fluids. Even before AIDS was a concern, however, the presence of other highly contagious infectious agents, such as hepatitis, justifiably caused serious concerns among health care workers and resulted in procedures and precautions being implemented for reducing this possible route of contamination. For industrial and laboratory workers handling toxic or hazardous materials, particularly persistent toxins such as mercury, lead and pesticides, extreme precautions are taken to avoid any worker exposure to these materials.

A second route is the transfer of contaminates from the user to the contaminatable object or materials being handled. Some types of computer and electrical components, such as disk drive storage media and halogen light bulbs, can be ruined by being merely touched with an unprotected hand. Detectable amounts of oil, moisture, skin flakes, etc. will inevitably be transferred to any object which is handled with an unprotected hand. Laboratory samples and crime scene evidence are two other types of materials that can easily be contaminated if proper protective hand coverings are not worn.

A third route for contamination is the transfer of contaminates from an earlier object handled by a worker to a later object handled by that worker or a co-worker. This third route is often the most difficult to control because the contamination may be indirect (i.e. it may not be directly from the earlier object to the worker to the later object).

Health care workers typically remove their old gloves and put on new gloves prior to examining or treating a new patient. What may be overlooked, however, is that when their gloves become contaminated during examination or treatment of a patient, any object touched by these gloves, such as a door handle, a pen, a drawer handle, or treatment equipment, may itself become contaminated. When handling particularly virulent infectious agents, an attempt may made to use cleaning or sterilizing agents, such as chemical solutions, to remove or neutralize contaminates which have been transferred to these areas. Remedial measures, such as applying cleaning or sterilizing agents, are typically less than completely effective in eliminating contamination. Similar issues arise when industrial or laboratory workers handle toxic, hazardous or contaminated materials. The preferred method for eliminating this route for contamination is to eliminate the contamination of these areas altogether.

A primary reason these areas become contaminated is the difficulty of removing and putting on typical hand coverings. Typical hand coverings require that the hand or a portion of the hand be place inside and positioned with respect to a closed section of the hand covering. It can take a greater part of a minute to remove a contaminated pair of conventional latex gloves, replace them with a new pair and properly position the new gloves over the user's hands. If after handling potentially contaminated materials, a health care worker must operate treatment equipment, the worker must first remove their current pair of gloves and then put on a new pair of gloves before handling the equipment. To avoid accidentally contaminating the patient with contaminates that may have been present on the machine, the worker must then remove this second pair of gloves and put on a third pair of gloves before again coming into contact with the patient.

In my U.S. Pat. No. 5,774,889, I describe a protective hand covering for adhering to a user's hand. In the preferred embodiment, a pressure-sensitive adhesive is applied to the back surface of a sheet of thin flexible film. The pressure-sensitive adhesive provides a sufficiently strong bond to prevent the hand covering from being inadvertently dislodged, but a sufficiently weak bond to allow the hand covering to be removed without injuring the user. The film is sufficiently impervious to contaminates to prevent the transfer of contaminates from the substance or object being handled to the user, and vice versa.

As disclosed in the '889 patent, the entire content of which is incorporated herein by reference, several methods for packaging and dispensing protective hand coverings are feasible. For example, a stack of protective hand coverings may be packaged in a tablet or fan-fold format. The hand coverings could also be dispensed from a continuous roll mounted in a holder. The importance of the dispenser is that by substantially decreasing the time it takes to remove and put on hand coverings, the time required to perform certain types of procedures can be dramatically reduced. Increasing the ease of putting on (and removing) hand coverings will also encourage workers to put on new hand coverings more frequently, which will in turn reduce the likelihood of indirect contamination.

In my U.S. Pat. No. 6,604,660, also incorporated herein by reference, I describe a dispenser for receiving a roll of thin, flexible film of the type described in my '889 patent. The dispenser includes a backing member over which film may be drawn from the roll through rotation such that the adhesive surface faces outwardly, enabling a user to place the palm and fingers of a hand against the film and backing member prior to severing the film into a sheet now adhered to the hand. The backing member itself preferably forms part of a compressible body enabling a user to squeeze the body through the film for improved adherence of the sheet to the hand.

Various mechanisms may be used alone or in combination to sever the film into an individual sheet. The sheet itself may include lines of perforations, spaced apart along the roll at a distance sufficient to cover a hand. Additionally, the dispenser may include an element which the film is drawn past to cut the film. Such an element may be in the form of a blade having a knife edge or serrations, and maybe heated. Depending upon the configuration, such an element may be between the backing member and the roll or on the other side of the backing member with respect to the roll.

The dispenser may further include a mechanism for preventing the roll from rotating while the film is severed into a sheet. Such a mechanism may also be coupled to the backing member. In the preferred embodiment, the backing member is moveable away from the roll, enabling a user to move the hand bearing against the film and backing member away from the roll to assist in severing the sheet from the roll.

SUMMARY OF THE INVENTION

The invention described herein resides in an improved dispenser for thin, flexible hand coverings of the type described in my U.S. Pat. No. 5,774,889. Unique to the present invention, the dispenser includes a mechanism to retain the opposing edges of the flexible film as it is advanced and applied to the hand, thereby promoting a controlled stretching, adherence and release.

In the preferred embodiment, the entrapment of the film edges is carried out using interlocking chains or other cooperative members that advance through guide channels. Another improvement is that the housing of the dispenser in this case is raised as the user pulls down the film to be adhered, and it is the weight of the dispenser that causes the unit to reset for the next use, thereby eliminating the need for springs, at least for this purpose.

BRIEF DESCRIPTION OF THE DRAWINGS

FIG. 5A is a side-view drawing that shows schematically how the edge of the film is trapped by interlocking chains;

FIG. 5B shows one form of interlocking belts that may be used to trap the film edges;

FIG. 5C shows an alternative form of interlocking belts;

FIG. 5D illustrates the use of two flexible magnetic belts (or one magnetic belt and a magnetically attractive belt); and FIG. 5E shows the use of two substantially flat belts with pressure applied to pinch the film edge.

DETAILED DESCRIPTION OF THE INVENTION

Figure 1:
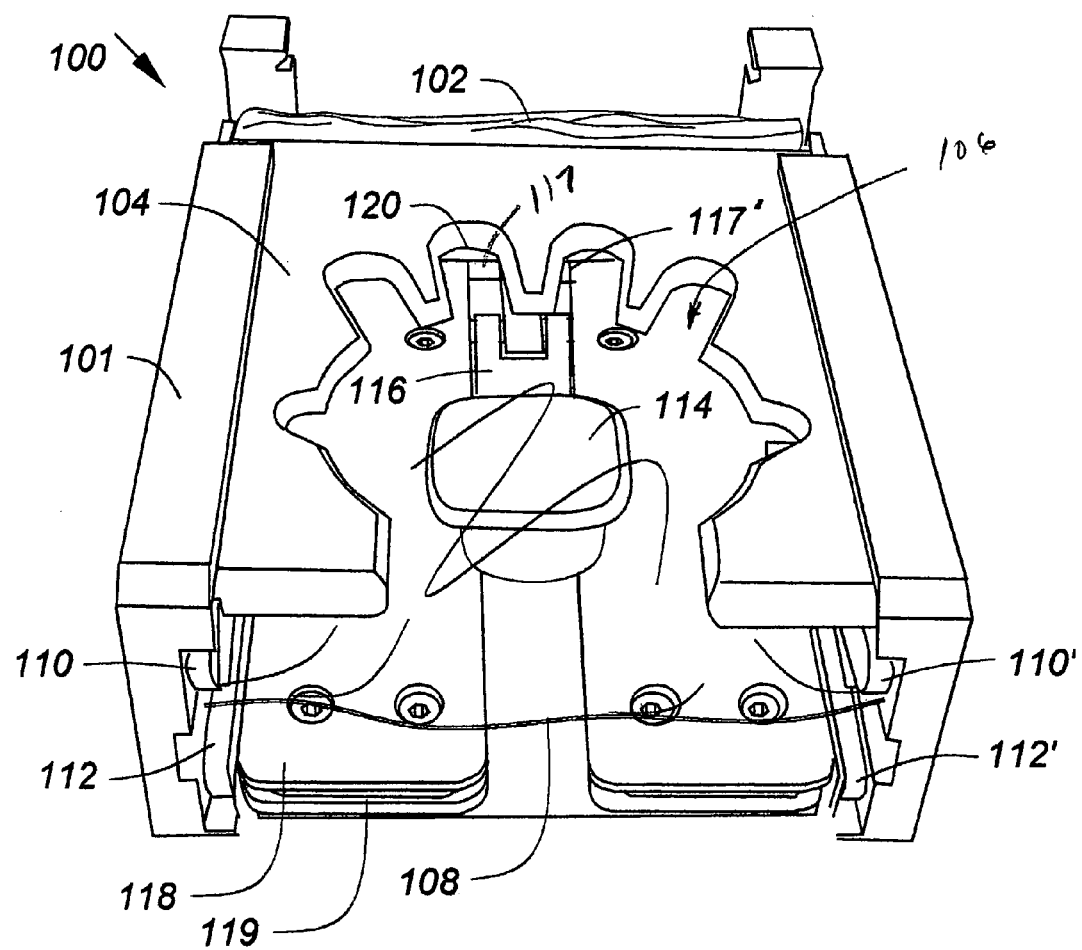
FIG. 1 is a perspective view of a preferred embodiment of the invention.

FIG. 1 depicts from an oblique perspective a preferred embodiment of the invention indicated generally at 100, with some of the outer shrouding removed to better illustrate various internal features of the dispenser. A roll of thin, flexible film to be used as a hand covering is shown at 102. Applicable films are described in U.S. Pat. No. 5,774,889, incorporated herein by reference. The film is drawn through the dispenser, with the right edge of the film being trapped between two chains 110', 112', and the left edge of the film being trapped between chains, 110, 112. The leading edge of the film is shown at 108, and the adhesive surface of the film faces outwardly.

Figure 3:
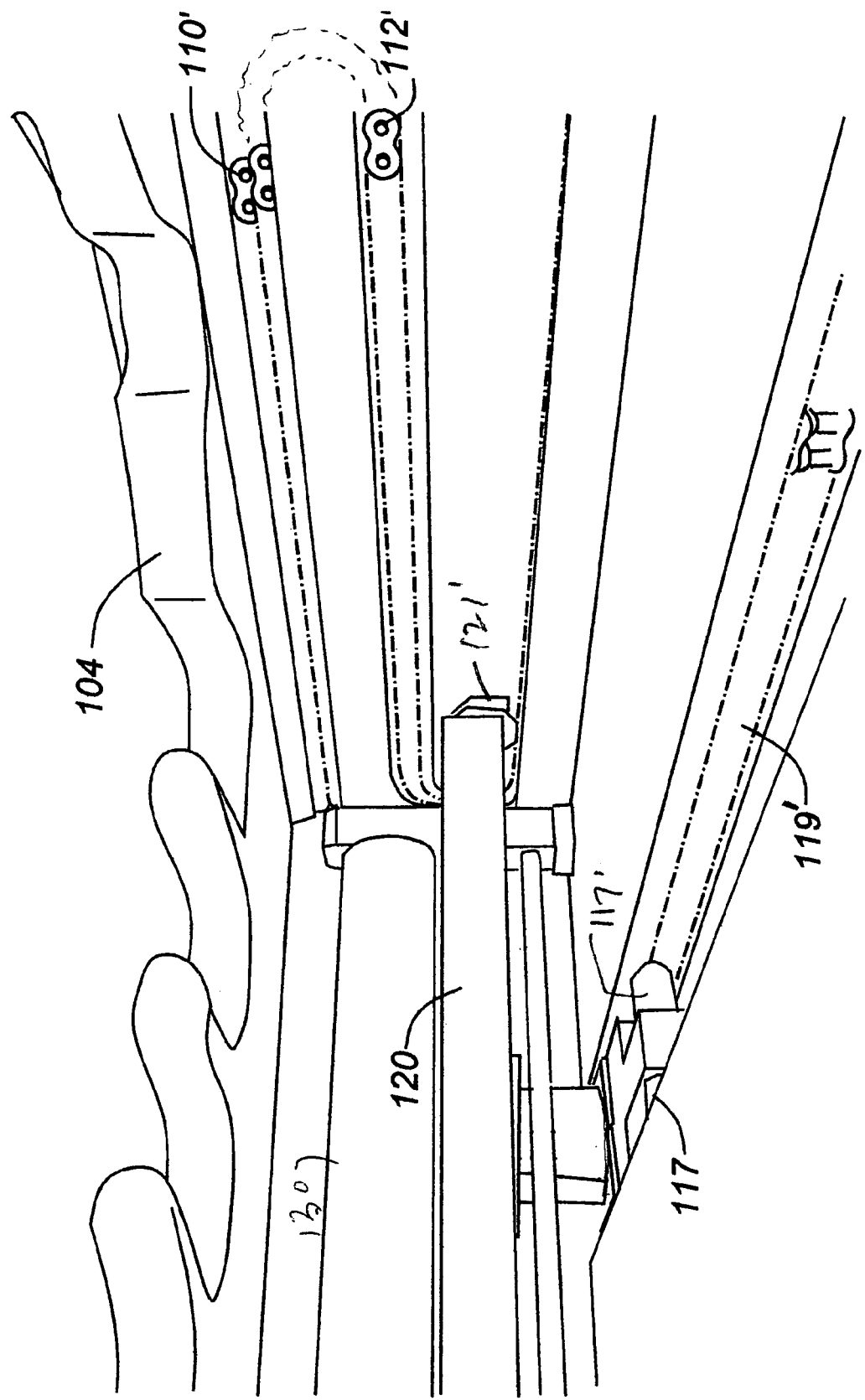
FIG. 3 is a close-up view of the way in which the interlocking chains engage.
Figures 4A, 4B, 4C:
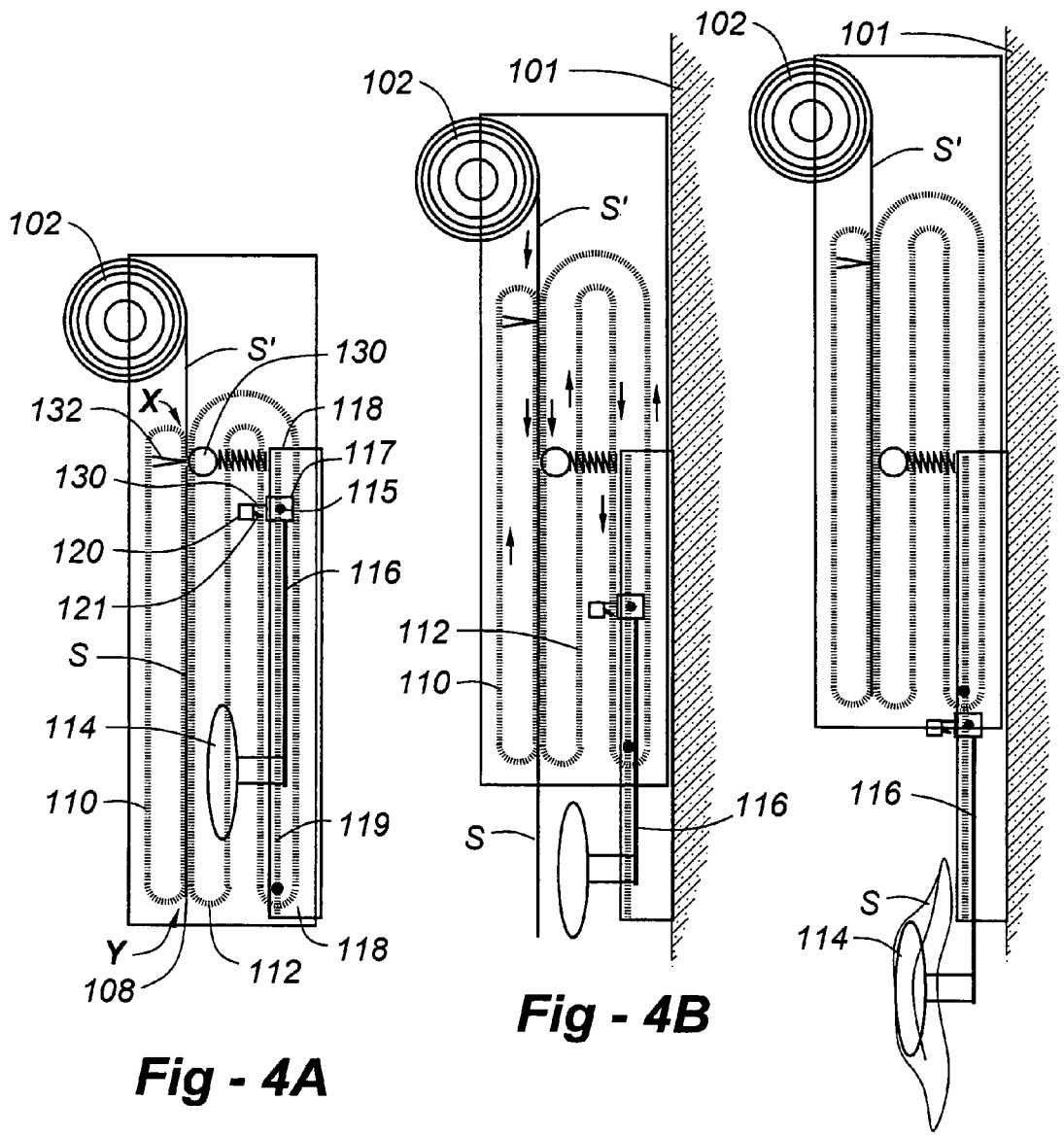
FIG. 4A is a schematic side view of a dispenser according to the invention, showing the disposition of certain features prior to use.
FIG. 4B is a schematic side view of the dispenser of FIG. 4A, showing the disposition of certain features prior to use.
FIG. 4C is a schematic side view of the dispenser of FIG. 4A, showing the disposition of certain features at full carriage extension prior to release.

Referring to FIG. 4A in particular, the film to be administered is fed into interlocking chains 110, 112, at point "X," and is retained as the chains and film travel in unison until released at point "Y." As better seen in FIG. 3, the chains travel in guide channels machined out of side members 101, 101' which are constructed of polyethylene or other suitable metallic or polymeric material. FIG. 5A is a side-view drawing that shows schematically how the edge of the film 500 is trapped by interlocking chains 502, 504. FIG. 5B shows one form of interlocking belts which may serve the same purpose. FIG. 5C shows an alternative form of interlocking belts. FIG. 5D illustrates the use of two flexible magnetic belts (or one magnetic belt and a magnetically attractive belt), and FIG. 5E shows the use of two substantially flat belts with pressure applied to pinch the film edge. Thus, although reference is made to "interlocking chains," it will be appreciated that this is not the only film-edge entrapment mechanism anticipated by the invention, and that "chains" should be taken to include at least these alternative mechanisms.

The film is held suspended in the dispenser between a compressible, graspable form 114 and an opening 106 formed into front panel 104. The opening 106 preferably shaped to guide either a right or left hand through the opening to gasp the form 114 through the film, thereby stretching the film over the form. Pulling down on the form 114 causes various actions, including the lifting of certain housing portions, the staging of a new sheet of film trapped between the opposing chain mechanisms, as well as the cutting of the new sheet. These details are perhaps better understood with reference to FIGS. 2 and 4A to 4B.

The form 114 connects to a linkage 116 which, in turn, connects to a device 117. The device 117 connects to chains 119, 119' at points 115, 115', and also connects to bar 120 through connector 113. Chains 119, 119' wind around respective portions 118, 118', which are connected and wall-mounted at point 134. The side members of the housing 101, 101' and also respectively connected to the chains 119, 119', such that as the form 114 and link 116 are pulled down, chains 119, 119' rotate around the portions 118 and 118', causing the enclosure and connected components to lift up as the user pulls down on the form 114 with the film adhered to the hand.

Figure 2:
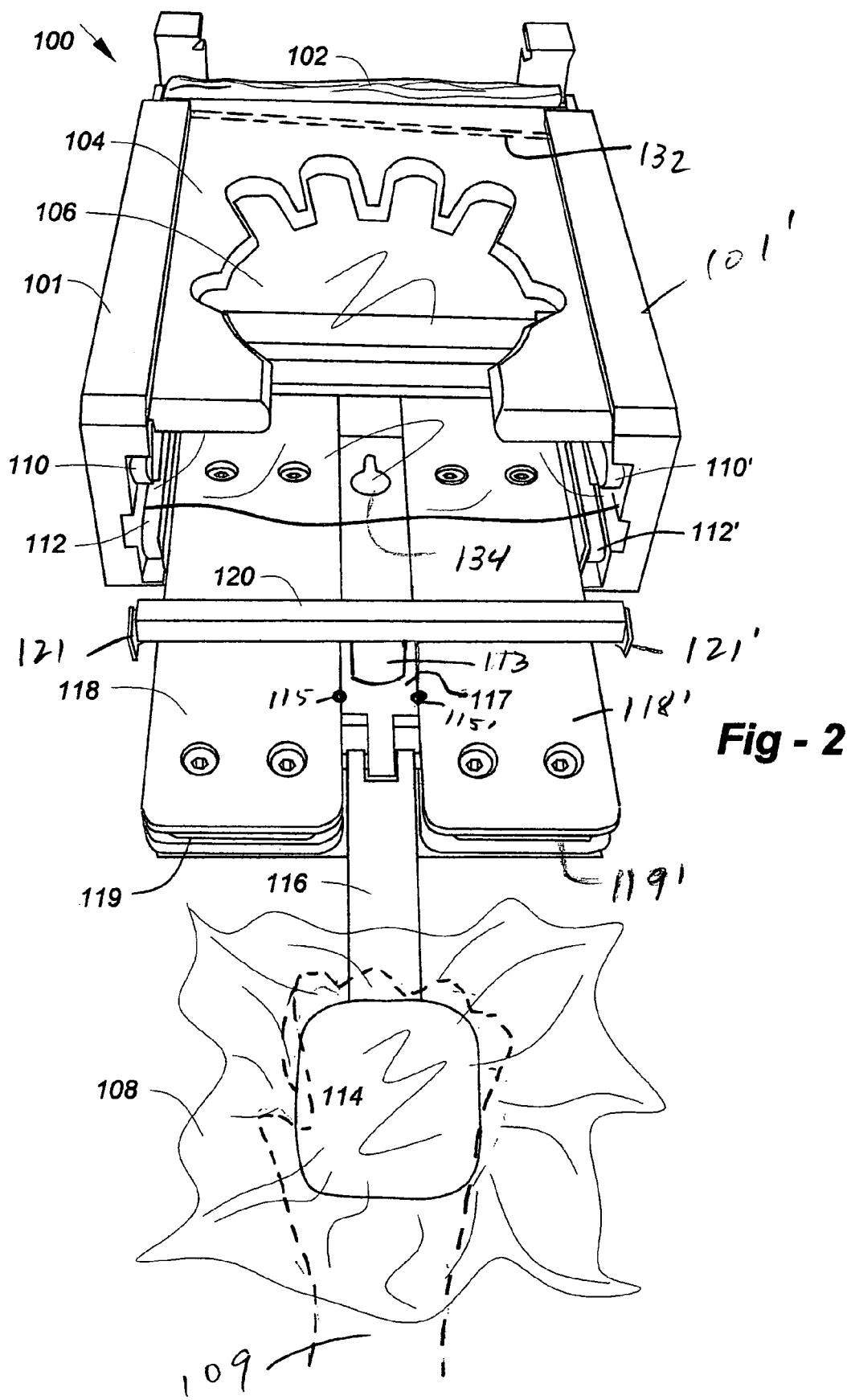
FIG. 2 is a perspective view of a portion of the preferred embodiment, taken from below to better illustrate a carriage mechanism.

FIG. 2 is a drawing of the dispenser 100 with the form 114 and link 116 pulled down, and over which a cut sheet of film 108 is disposed. The user's hand grasping the form 114 to apply the adhesive side of the film 108 to the hand is shown in broken line form at 109. Note that with the portions 118, 118' wall-mounted, the body of the enclosure, including side members 101, 101', panel 104, and chains 110, 112, 110', 112' are raised up as the form is pulled down. This action will perhaps be better understood in conjunction with the schematic diagrams of FIGS. 4A-C.

The chains 119, 119' also connect to a bar 120 through device 117 and connector 113. The bar includes tabs 121, 121' on either side which engage with chains 112, 112' which travel through a serpentine path on either side of the enclosure. As bar 120 moves downwardly with the form 114 and link 116, this causes the chains 112, 112' to rotate as well, at least until the bar 120 and tabs 121, 121' extend past the bottom of the enclosure. During rotation of the chains 112, 112', however, the next sheet of flexible film is drawn from the roll and indexed into position.

FIG. 3 better illustrates how one of the tabs 121' temporarily engages with a chain (112'), and how opposing arms 117, 117' are linked to chain 119 for the purpose of lifting the dispenser housing. Although the tabs 121, 121' may be spring-loaded, they are slightly rotatable and shaped such that gravity causes them to automatically ratchet and re-engage with the chains 112, and 112' as the enclosure falls back into position.

To cut the film, a spring-loaded roller 130 rolls past a cutting blade 132, shown schematically in FIG. 4A. The blade fits into a diagonally oriented groove including a retainer enabling authorized personnel to change/maintain the blade. The roller 130 is linked to the wall mounted portions, whereas the blade 132 is connected to the housing portions which rise up during use. Thus, although the roller effectively "remains in place," relative movement between roller and blade exists to sever each sheet from the roll. Indeed, each sheet of film is actually cut twice: once when the enclose falls back into position, causing the roller to roll up and past the blade, and a second time when the form 114 is initially pulled down. Since the blade is oriented on an angle, at any time there is only one point of contact between the blade and the roller, such that any imperfections in the roller or the blade are inconsequential in the sense that the system automatically resets to maintain cutting action in the event of an imperfection or void.

FIGS. 4A-4C are simplified, side-view diagrams of a preferred embodiment of the invention, perhaps better illustrating the way in which the various mechanisms operate during use. FIG. 4A shows the status of the dispenser with a sheet having a forward edge 108 in position, trapped between chains 110 and 112, and having been cut initially by roller 130 riding against blade 132. The roll of hand covering is shown at 102, and the base portion 118, being adhered to side member 101 shown in FIGS. 4B and 4C.

The form 114 is shown schematically connecting to link 116 which connects to device 117. Device 117 is shown schematically connecting to chain 119 that winds around wall-mounted form 118, and to bar 120 through connector 130, with one of the side tabs engaging with chain 112, being shown at 121.

In FIG. 4B, the form 114 has been pulled down somewhat, causing sheet S to move in unison. The chains 110 and 112 also move in the directions shown due to the engagement of tab 121 with chain 112. Note that a next sheet, S2, is being drawn off the roll 102, also due to the relative movement of chains 110, 112. In FIG. 4C, the chains 110, 112 no longer move, as the bar 120 and tab 121 have now been moved entirely from these chains. However, the bulk of the enclosure continues to move upwardly relative to the side member 101, since the body 117, connected to chain 119 at point 115, continues to cause that chain to rotate around the form 118. This sheet S is shown molded around form 114, though the hand of the user is not shown. Form 114, through link 116, will continue to move down, with the bulk of the enclosure continuing to move up, until the user lets go, at which time the enclosure will move down, and the form 114 and link 116 will move up, to regain the position shown in FIG. 4A, ready for the next use.

Although a system has been described wherein the pulling down on a form causes the rotation of interlocking chains or other cooperative members through dedicated linkage (link 116, device 117, connector 113, bar 120 and ratcheting tabs 121, 121'), in an alternative embodiment the film itself may be used as the pulling mechanism. That is, assuming the film it sufficiently strong and that the interlocking chains or other cooperative members rotate freely enough, the tension of the film alone may be adequate to cause the rotation of the chains or other members without the need for an additional connection. In such a case, a simpler arrangement of chain 112, 112' may be possible, such as the simple loop of chain 110, 110'. In this and in other embodiments, the film may be cut within the enclosure or pre-cut (i.e., perforated), though registration of the perforations would be a consideration.

The invention claimed is:

1. A dispenser for a hand covering, comprising:
    a housing to receive a roll of thin, flexible film having opposing side edges to be used as a hand covering;
    a form configured to be grasped by a user through the film such that the film temporarily clings to the user's hand; and
    a set of interlocking chains or opposing belts on either side of the housing to retain the side edges of the film as it moves through the dispenser for each use.

2. The dispenser of claim 1, further including a cutter to cut the film into individual sheets.

3. The dispenser of claim 1, wherein:
    the form is connected to a pull-down mechanism that lifts a portion of the housing during use; and
    the weight of the housing falling back into position is responsible for resetting the dispenser for the next use thereof.

4. The dispenser of claim 1, further including a hand-shaped opening to assist a user in grasping the form.

5. A dispenser, comprising:
    a roll of thin, flexible film having opposing side edges and an adhesive surface to be used as a hand covering;
    a form configured to be grasped by a user through the film with the adhesive surface facing outwardly such that the film temporarily adheres to the user's hand; and
    a set of interlocking chains or opposing belts on either side of a housing to retain the side edges of the film as it moves through the dispenser for each use.

6. The dispenser of claim 5, further including a cutter to cut the film into individual sheets.

7. The dispenser of claim 5, wherein:
    the form is connected to a pull-down mechanism that lifts a portion of the housing during use; and
    the weight of the housing falling back into position is responsible for resetting the dispenser for the next use thereof.

8. The dispenser of claim 5, further including a hand-shaped opening to assist a user in grasping the form.

* * * * *